(12) United States Patent
Wiggins

(10) Patent No.: US 7,663,367 B2
(45) Date of Patent: Feb. 16, 2010

(54) SHAPED MRI COIL ARRAY

(75) Inventor: Graham C. Wiggins, Lynn, MA (US)

(73) Assignee: The General Hospital Corporation, Boston, MA (US)

( * ) Notice: Subject to any disclaimer, the term of this patent is extended or adjusted under 35 U.S.C. 154(b) by 188 days.

(21) Appl. No.: 11/839,248

(22) Filed: Aug. 15, 2007

(65) Prior Publication Data

US 2008/0007250 A1  Jan. 10, 2008

Related U.S. Application Data

(63) Continuation-in-part of application No. 11/579,576, filed as application No. PCT/US2005/015342 on May 3, 2005, now abandoned.

(51) Int. Cl.
G01V 3/00 (2006.01)
A61B 5/055 (2006.01)

(52) U.S. Cl. .................. 324/318; 324/309; 600/410; 600/422

(58) Field of Classification Search ......... 324/300–322; 600/410, 411, 422, 423; 333/219–235
See application file for complete search history.

(56) References Cited

U.S. PATENT DOCUMENTS

| | | | |
|---|---|---|---|
| 4,825,162 | A | 4/1989 | Roemer et al. |
| 6,534,983 | B1 * | 3/2003 | Boskamp et al. ............ 324/318 |
| 7,449,888 | B1 * | 11/2008 | Malik et al. ................ 324/318 |
| 7,570,054 | B1 * | 8/2009 | Lin ............................ 324/309 |
| 2002/0156362 | A1 | 10/2002 | Bock et al. |
| 2003/0100826 | A1 | 5/2003 | Savelainen |
| 2007/0013377 | A1 * | 1/2007 | Wosik et al. ................ 324/322 |
| 2007/0282194 | A1 * | 12/2007 | Wiggins et al. ............. 600/422 |
| 2008/0007250 | A1 * | 1/2008 | Wiggins ...................... 324/200 |
| 2008/0103383 | A1 * | 5/2008 | van der Kouwe et al. ... 600/410 |
| 2008/0272782 | A1 * | 11/2008 | Lin ............................ 324/312 |
| 2009/0179643 | A1 * | 7/2009 | Lin ............................ 324/312 |

FOREIGN PATENT DOCUMENTS

WO  WO 2004038431 A2 *  5/2004
WO  WO 2005109010 A2 * 11/2005

OTHER PUBLICATIONS

PCT/US05/15342 Search Report under date of mailing of Dec. 21, 2005.

* cited by examiner

*Primary Examiner*—Brij B. Shrivasatav
*Assistant Examiner*—Tiffany A Fetzner
(74) *Attorney, Agent, or Firm*—Quarles & Brady LLP

(57) ABSTRACT

An MRI rf coil array is comprised of a large number of separate coil elements that are supported on a substrate that is shaped to the contour of the anatomy being imaged. The coil elements overlap each other to reduce mutual inductance and their location is determined by tiling the surface of the substrate with regular, substantially same sized polygons. The center of each coil element is aligned with the center of a polygon. By using a mixture of different polygons, such as hexagons and pentagons, an arrangement of coil elements may be formed that cover a surface with non-zero Gaussian curvature where each coil is overlapped with its neighbors such that their mutual inductance is nulled.

33 Claims, 12 Drawing Sheets

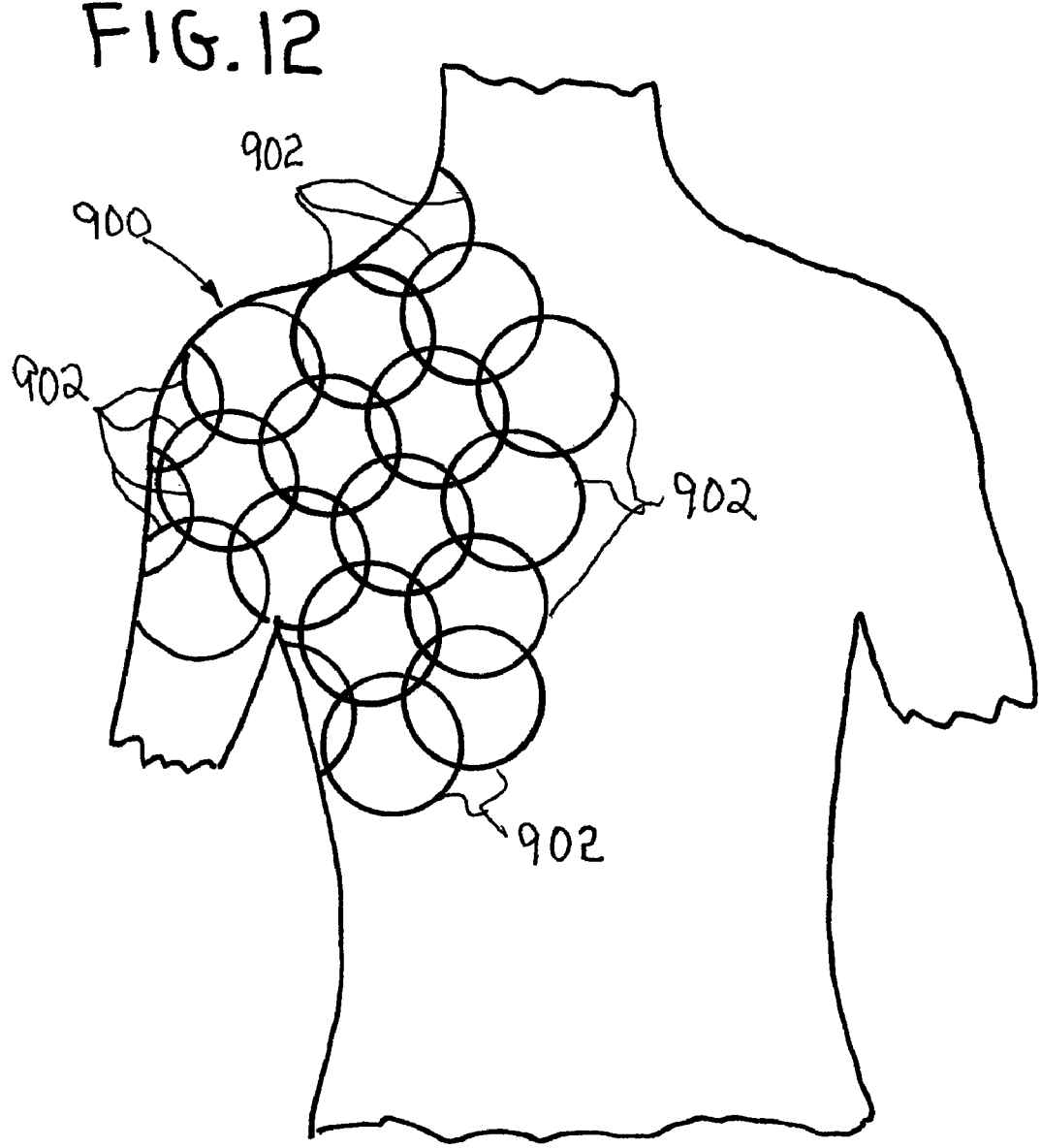

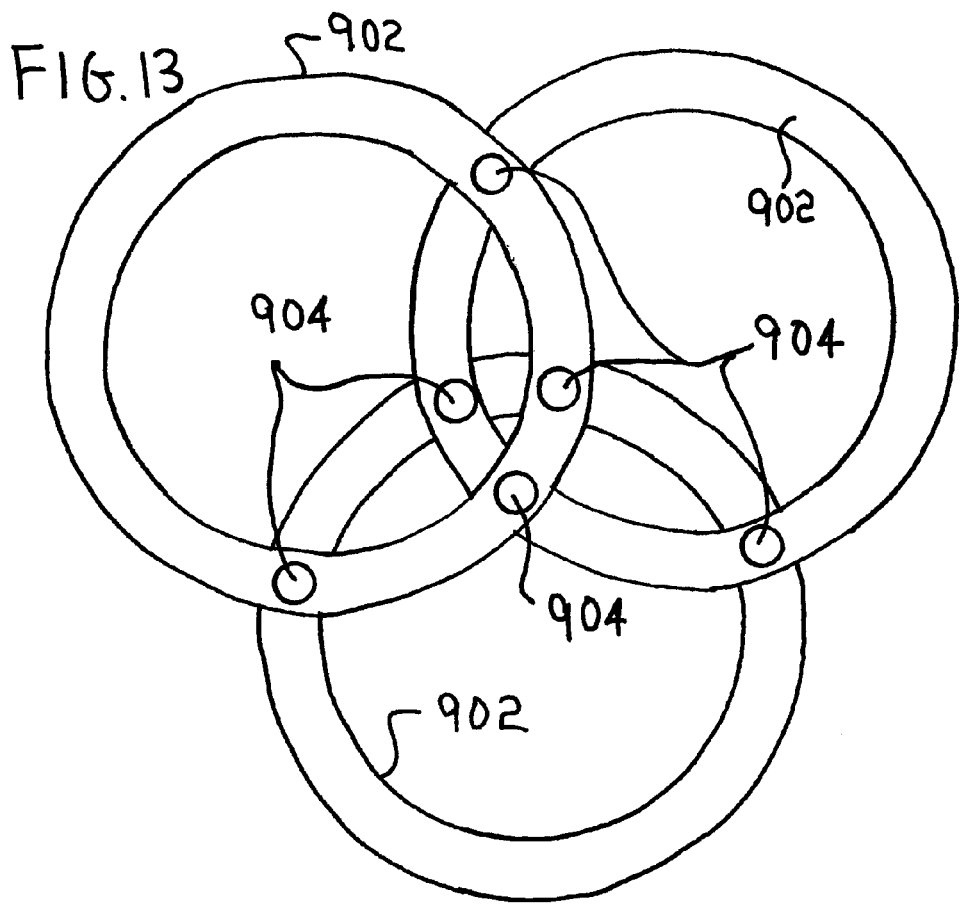
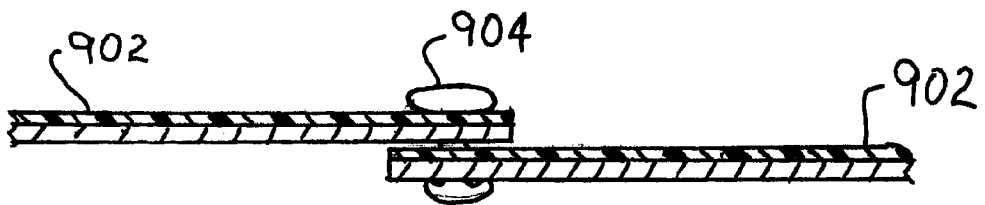

SHAPED MRI COIL ARRAY

CROSS-REFERENCE TO RELATED APPLICATIONS

This application is a continuation-in-part of U.S. patent application Ser. No. 11/579,576 filed Nov. 2, 2006 now abandoned, which claims the benefit of International Application No. PCT/US2005/015342 filed on May 3, 2005 and U.S. Provisional Application No. 60/568,035, filed May 3, 2004.

BACKGROUND OF THE INVENTION

The field of the invention is nuclear magnetic resonance imaging MRI methods and systems. More particularly, the invention relates to the design and manufacture of multi-element coil arrays for use in MRI systems.

When a substance such as human tissue is subjected to a uniform static magnetic field (polarizing field $B_0$), the individual magnetic moments of the spins in the tissue attempt to align with this polarizing field, but precess about it in random order at their characteristic Larmor frequency. If the substance, or tissue, is subjected to a time-varying magnetic field (excitation field $B_1$) which is in the x-y plane and which is near the Larmor frequency, the net aligned moment, $M_z$, may be rotated, or "tipped", into the x-y plane to produce a net transverse magnetic moment $M_t$. A signal is emitted by the excited spins after the excitation signal $B_1$ is terminated, this signal may be received and processed to form an image.

When utilizing these signals to produce images, magnetic field gradients ($G_x$, $G_y$ and $G_z$) are employed. Typically, the region to be imaged is scanned by a sequence of measurement cycles in which these gradients vary according to the particular localization method being used. The resulting set of received NMR signals also referred to as "views" are digitized and processed to reconstruct the image using one of many well known reconstruction techniques.

The NMR signals are detected using an rf antenna in the form of one or more rf coils. MRI systems include a whole-body rf coil that can receive NMR signals emanating from anywhere in a subject being imaged, but it is also common practice to use specially designed local rf coils when imaging specific anatomy. These local coils are positioned very close to the anatomy being imaged and the result is an increased sensitivity to the NMR signals and a consequent higher SNR in the image reconstructed from those signals.

While single element local coils are used in some clinical applications, because of their limited receptivity field it is also common practice to employ multi-element rf coil arrays. Each coil element operates as a separate rf antenna and is connected to a separate receive channel in the MRI system. The separate NMR signals are combined to increase the receptivity field of view to that of the combined rf coil elements.

When using an array of rf coils to receive NMR signals from a subject being examined, there are two design objectives that should be met to maximize coil sensitivity. First, the coil elements in the array should follow as closely as possible the contour of the subject being imaged, and second, the mutual inductance between each rf coil element in the array should be minimized to reduce interaction between receive channels.

Many multi-element rf coil array designs are based on the overlapping coil element design first disclosed in U.S. Pat. No. 4,825,162 issued on Apr. 25, 1989 and entitled "Nuclear Magnetic Resonance "NMR" Imaging With Multiple Surface Coils". Multiple flat rf coil elements are placed next to one another to cover the desired field of view in the subject and mutual inductance between adjacent coil elements is minimized by carefully overlapping adjacent coil elements a specified amount. Coil elements can be arranged in a row, with each coil element overlapping the next one by the critical amount to form a linear array (such as a spine array). Additional rows of coil elements can be arranged next to each other overlapping in the second dimension to produce a planar array. Such a planar array can be curved into a shape having one dimension of curvature (i.e., curving along only one dimension). For example, a linear or planar array can be wrapped around to form a cylinder. It is easy to maintain the required coil element overlap when the coil array is substantially flat or is curved in only one direction (e.g., cylindrical), but when the anatomy being imaged requires a more complex curvature, it is difficult to maintain the desired coil element overlap. Such complex curved surfaces are referred to herein as surfaces having non-zero Gaussian curvature. This means that the surface curves in all directions from at least one point on the surface.

A number of factors are driving the number of coil elements in rf coil arrays upward. The sensitivity of a single circular receive element achieves the maximum possible sensitivity at a depth equal to the element diameter divided by the square root of 5. A large array of receive elements is able to achieve the maximum possible sensitivity at any depth greater than the single element diameter divided by the square root of 5. By reducing the size of each coil element, increasing the number of substantially planar coil elements and shaping the array to more closely follow the contour of the anatomy being imaged the array can achieve close to the optimum possible sensitivity throughout the volume enclosed by the array. This increases coil sensitivity and image SNR. Another factor is the use of parallel imaging methods such as SENSE (U.S. Pat. No. 6,326,786), and GRAPPA (U.S. Pat. No. 6,841,998). Parallel imaging uses the separate NMR signals from rf coil arrays to reduce the number of views that are required to reconstruct an image. Hence, the larger the number of coil elements and corresponding receive channels used, the shorter the scan time.

The design and manufacture of coil arrays having larger numbers of coil elements and complex curvatures while maintaining minimum mutual inductance between coil elements has become a very challenging task.

SUMMARY OF THE INVENTION

The present invention is an MRI rf coil array for use in applications where a complex curvature is desired to conform to the shape of a subject to be imaged. More specifically, it includes a substrate formed to have the desired shape and a plurality of coil elements mounted on the surface of the substrate in an overlapping pattern. The overlapping pattern is based on a tiling pattern of regular polygons that cover the surface of the substrate and each coil element is aligned around a center of one of said regular polygons and is sized to overlap adjacent coil elements such that the mutual inductance there between is minimized.

A general object is to provide a coil array that conforms to a complex surface having a Gaussian curvature which is non-zero. By tiling the complex surface with regular polygons of substantially the same size, corresponding coil elements can be located and sized to follow the complex surface and minimize mutual inductance. Polygons with fewer sides are used at points of higher curvature. Specifically, the incorporation of pentagons into an array of hexagons allows for coil elements of substantially the same size to be arranged on a surface with Gaussian curvature while maintaining the critical overlap between all neighboring coils such their mutual inductance is minimized.

Another aspect of the present invention is a design which prevents the increase in coupling that occurs with small coil elements. When the coil elements are very small (on the order of 2 inches diameter or less) the capacitor value needed for matching the sample impedance to the 50 Ohm system becomes large. When this capacitor is also used as the basis for the coil decoupling circuit it results in a low Q decoupling circuit, which reduces the strength of the preamp decoupling effect. Even though neighboring coils are overlapped, there is significant coupling between next nearest neighbors, and when preamp decoupling is weak this leads to a loss in sensitivity. The present invention addresses this problem by separating the match functionality and detuning functionality to create a high Q decoupling circuit which results in a stronger preamp decoupling effect, increasing the sensitivity of the receive array.

Yet another aspect of the present invention is the construction of a high Q coil element for a coil array. It is recognized that for a coil element constructed from a flat strip conductor such as machined circuit board or flexible Pyralux circuit board material, if the track width is kept the same, as the number of coil elements in an array increases and their size decreases, the percentage of copper covering the surface increases. The copper in the other coil elements creates a loading effect on each coil element, reducing the unloaded Q and adding noise. It has been discovered that by manufacturing the coil element with a substantially round wire instead of the conventional printed circuit board ribbon conductor, this drop in unloaded Q is ameliorated.

Another aspect of the invention is the incorporation of a circuit between the preamp and the coil element which allows any given element to couple with the transmit B1 RF field in a controlled way to allow flexible reshaping of the transmit B1 field.

Another aspect of the present invention is a method of manufacturing a multi-element coil array that has a non-zero Gaussian curvature. A pattern having a plurality of polygonal coil element circuit board patterns is formed on a flexible substrate which is then folded, or formed, into the desired shape. The circuit board patterns on adjacent polygonal patterns are connected together to form an array of overlapping coil elements.

The invention is used in connection with MRI scanners. It may include a helmet-type coil covered with surface coil elements each of which can both transmit and receive an RF signal at the operating frequency of the scanner. It may also include a larger helmet-like structure which only creates a transmit $B_1$ field and has separate receive coils within it. It requires additional hardware to control the RF signal fed to each coil element, either by adjusting the phase and amplitude of the signal to each element or by sending different RF waveforms to each element as with Transmit SENSE. The device allows greater homogeneity of the $B_1$ field in high field MRI, or for focused RF excitation of only particular regions of interest to reduce the overall SAR load in the subject.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 12 is a pictorial view of another embodiment of a coil array made according to the present invention;

FIG. 13 is a partial pictorial view of the coil array in FIG. 12; and

FIG. 14 is a partial view in cross-section of a part of the coil array of FIG. 12.

DETAILED DESCRIPTION OF THE PREFERRED EMBODIMENT

Figure 1:
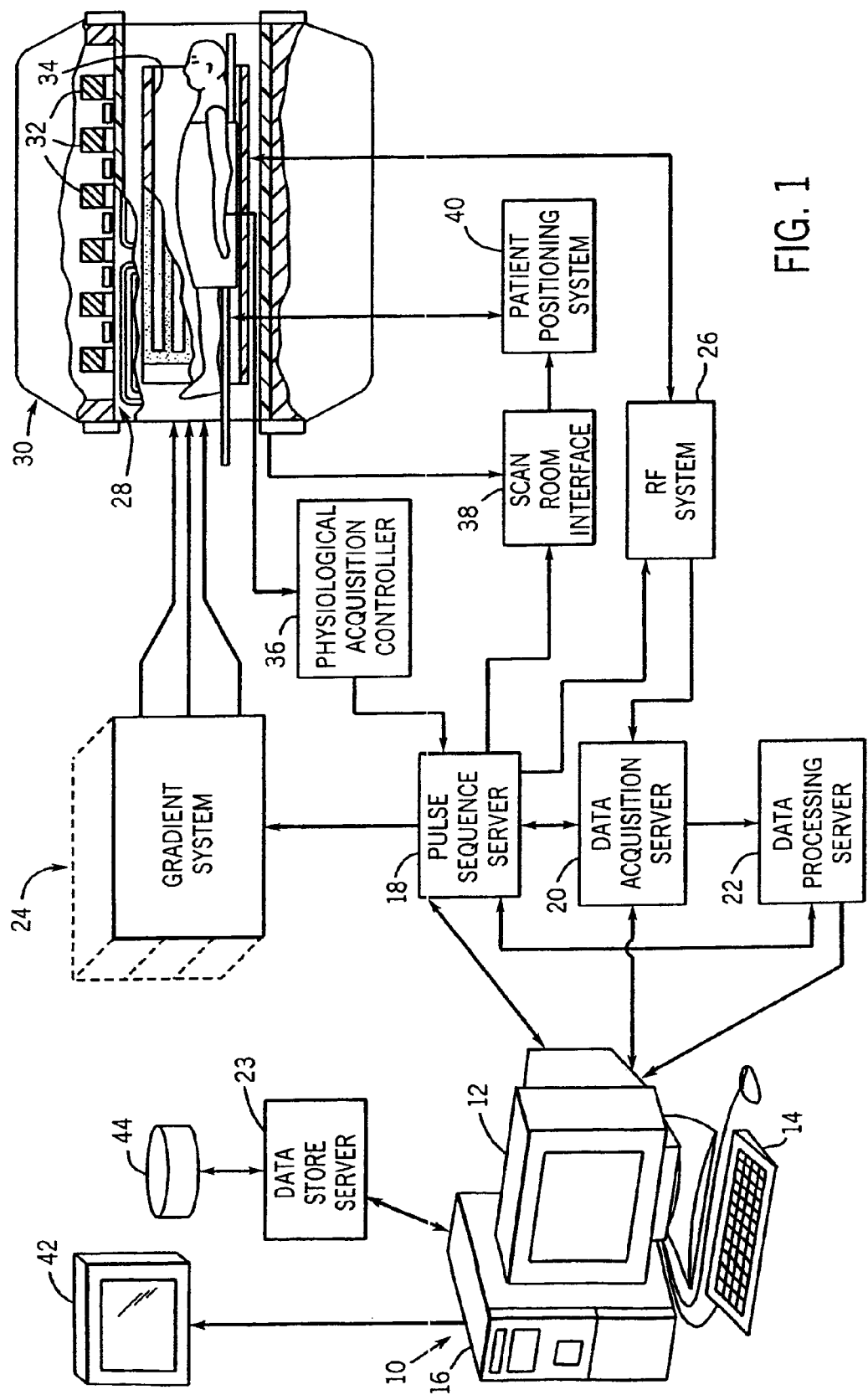
FIG. 1 is a block diagram of an MRI system which employs the present invention.

Referring particularly to FIG. 1, the preferred embodiment of the invention is employed in an MRI system manufactured by Siemens Medical Solutions of Erlangen, Germany (3T Tim Trio). The MRI system includes a workstation 10 having a display 12 and a keyboard 14. The workstation 10 includes a processor 16 which is a commercially available programmable machine running a commercially available operating system. The workstation 10 provides the operator interface which enables scan prescriptions to be entered into the MRI system.

The workstation 10 is coupled to four servers: a pulse sequence server 18; a data acquisition server 20; a data processing server 22, and a data store server 23.

The pulse sequence server 18 functions in response to program elements downloaded from the workstation 10 to operate a gradient system 24 and an RF system 26. Gradient waveforms necessary to perform the prescribed scan are produced and applied to the gradient system 24 which excites gradient coils in an assembly 28 to produce the magnetic field gradients $G_x$, $G_y$ and $G_z$ used for position encoding NMR signals. The gradient coil assembly 28 forms part of a magnet assembly 30 which includes a polarizing magnet 32 and a whole-body RF coil 34.

RF excitation waveforms are applied to the RF coil 34 by the RF system 26 to perform the prescribed magnetic resonance pulse sequence. Responsive NMR signals detected by a separate RF coil array described below are received by the RF system 26, amplified, demodulated, filtered and digitized under direction of commands produced by the pulse sequence server 18. The RF system 26 includes an RF transmitter for producing a wide variety of RF pulses used in MR pulse sequences. The RF transmitter is responsive to the scan prescription and direction from the pulse sequence server 18 to produce RF pulses of the desired frequency, phase and pulse amplitude waveform.

The RF system 26 also includes a plurality of RF receiver channels. In the preferred embodiment 90 receiver channels are employed. Each RF receiver channel includes an RF amplifier that amplifies the NMR signal received by the coil to which it is connected and a quadrature detector which detects and digitizes the I and Q quadrature components of the received NMR signal. The magnitude of the received NMR signal may thus be determined at any sampled point by the square root of the sum of the squares of the I and Q components:

$$M=\sqrt{I^2+Q^2},$$

and the phase of the received NMR signal may also be determined:

$$\phi=\tan^{-1} Q/I.$$

The pulse sequence server 18 also optionally receives patient data from a physiological acquisition controller 36. The controller 36 receives signals from a number of different sensors connected to the patient, such as ECG signals from electrodes or respiratory signals from a bellows. Such signals are typically used by the pulse sequence server 18 to synchronize, or "gate", the performance of the scan with the subject's respiration or heart beat.

The pulse sequence server 18 also connects to a scan room interface circuit 38 which receives signals from various sensors associated with the condition of the patient and the magnet system. It is also through the scan room interface circuit 38 that a patient positioning system 40 receives commands to move the patient to desired positions during the scan.

The digitized NMR signal samples produced by the RF system 26 are received by the data acquisition server 20. The data acquisition server 20 operates to receive the real-time NMR data and provide buffer storage such that no data is lost by data overrun. In some scans the data acquisition server 20 does little more than pass the acquired NMR data to the data processor server 22. However, in scans which require information derived from acquired NMR data to control the further performance of the scan, the data acquisition server 20 is programmed to produce such information and convey it to the pulse sequence server 18. For example, during prescans NMR data is acquired and used to calibrate the pulse sequence performed by the pulse sequence server 18. Also, navigator signals may be acquired during a scan and used to adjust RF or gradient system operating parameters or to control the view order in which k-space is sampled. And, the data acquisition server 20 may be employed to process NMR signals used to detect the arrival of contrast agent in an MRA scan. In all these examples the data acquisition server 20 acquires NMR data and processes it in real-time to produce information which is used to control the scan.

The data processing server 22 receives NMR data from the data acquisition server 20 and processes it in accordance with the image reconstruction method of the present invention. Images reconstructed by the data processing server 22 are conveyed back to the workstation 10 where they are stored. Real-time images may be output to operator display 12 or a display 42 which is located near the magnet assembly 30 for use by attending physicians. Batch mode images or selected real time images are stored in a host database on disc storage 44. The workstation 10 may be used by an operator to archive the images, produce films, or send the images via a network to other facilities.

Figure 4:
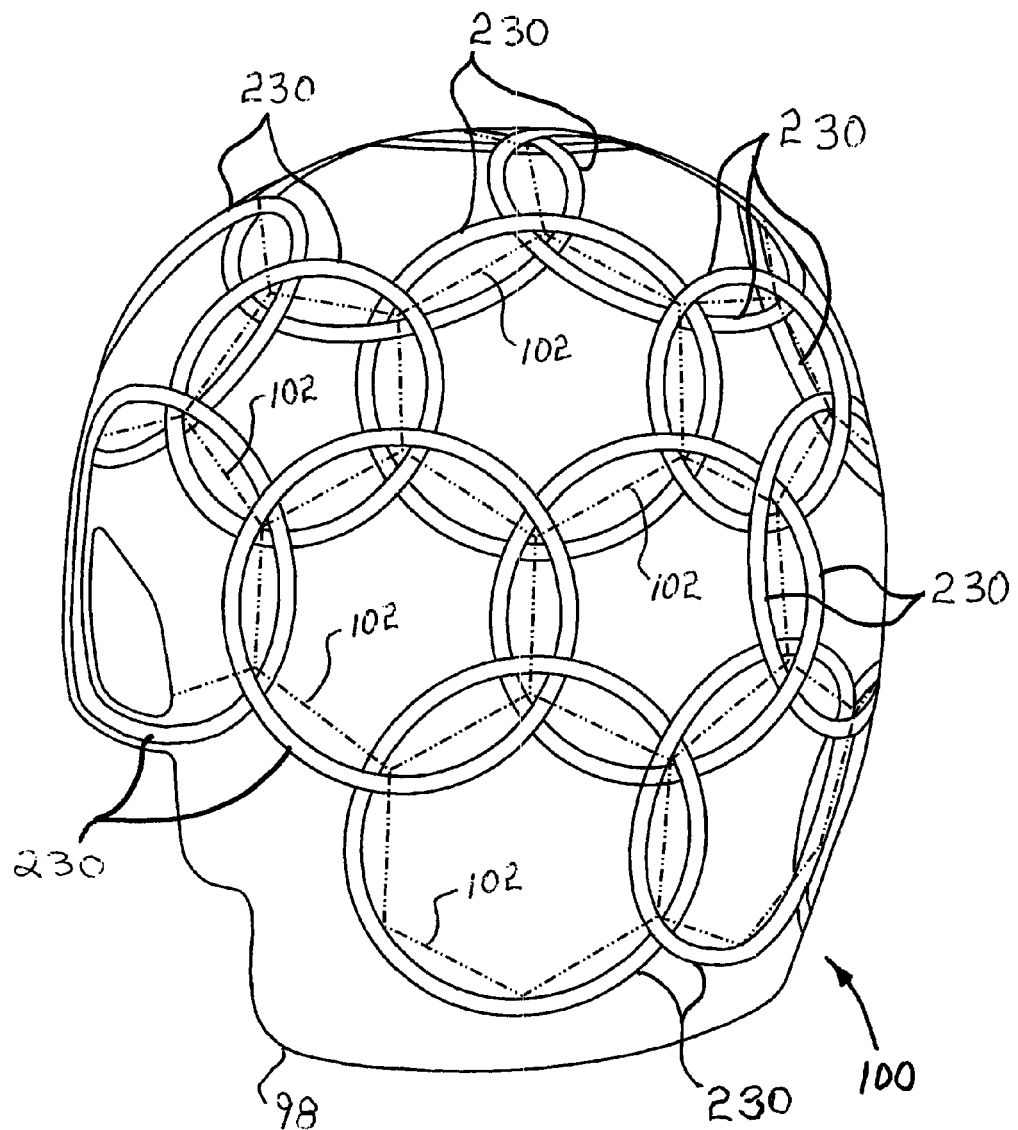
FIG. 4 is a pictorial view of a preferred embodiment of the coil array of FIG. 2.

Referring particularly to FIG. 4, in one embodiment of the invention which is used to acquire images from the human brain a coil array 100 in the shape of a helmet 98 is used to receive NMR signals. It is placed on the subject's head and connected to the RF system 26 as will be described in detail below. The close-fitting fiberglass helmet 98 is modeled after the European head standard form EN960/1994 for protective headgear. This coil array 100 has separate rf coil elements 230 which are supported by the curved helmet surface that acts as a substrate. Each coil element is substantially circular in shape and adjacent coil elements overlap such that their mutual inductance is minimized. The cable length leading from each of the coil elements 230 to the preamplifier in its corresponding receiver channel is carefully chosen and the tuning of the matching circuit to the preamplifier is chosen to transform the preamplifier input impedance to a low impedance across the circular coil element 230. An arrangement of hexagonal and pentagonal tiles (indicated by dashed lines 102 in FIG. 4) cover the helmet surface, similar to a truncated icosahedron or "soccer ball". Each tile 102 has sides that are approximately 40 mm long and a circular surface coil 230 is centered on each one of the tiles 102. Each surface coil 230 is made from Pyralux flexible circuit board with a conductor width of 5 mm. The diameter of each coil element ranges from 8.5 cm to 6.0 cm. It has been found that significant 5 to 8-fold gains in SNR are possible with this structure as compared to conventional head coils, particularly in the cerebral cortex. This embodiment is preferred for head coils having from 8 to 56 coil elements 230, where as coil elements constructed of circular-shaped wire as described in more detail below is preferred for head coils having more than 56 coil elements 230.

Figure 2:
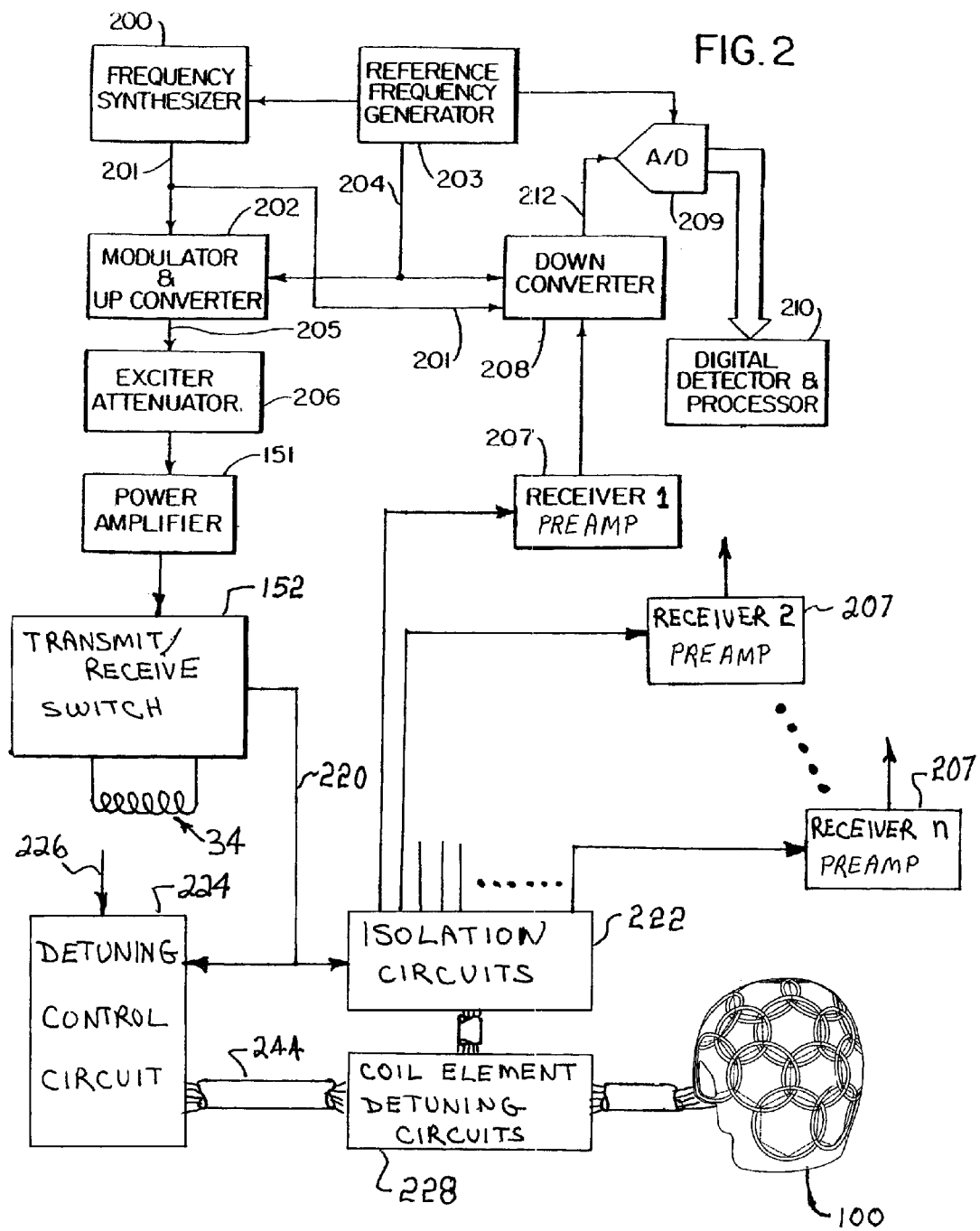
FIG. 2 is a block diagram of the RF system that forms part of the MRI system of FIG. 1.

Referring particularly to FIG. 2, the RF system 26 includes a transmitter that produces a prescribed rf excitation field. The base, or carrier, frequency of this RF excitation field is produced under control of a frequency synthesizer 200 which receives a set of digital signals from the pulse sequence server 18. These digital signals indicate the frequency and phase of the RF carrier signal produced at an output 201. The RF carrier is applied to a modulator and up converter 202 where its amplitude is modulated in response to a signal R(t) also received from the pulse sequence server 18. The signal R(t) defines the envelope of the RF excitation pulse to be produced and is produced by sequentially reading out a series of stored digital values. These stored digital values may, be changed to enable any desired RF pulse envelope to be produced.

The magnitude of the RF excitation pulse produced at output 205 is attenuated by an exciter attenuator circuit 206 which receives a digital command from the pulse sequence server 18. The attenuated RF excitation pulses are applied to the power amplifier 151 that drives the RF coil 34 through a transmit/receive switch 152.

Referring still to FIG. 2 the NMR signals produced by the subject are picked up by coil array 100 and applied to the inputs of receive channels. The number of receive channels corresponds to the number of separate rf coil elements 230 in the coil array 100. Each receive channel includes a preamplifier 207 that serves as the input to the receive channel and that amplifies the NMR signal produced by one coil element 230 by an amount determined by a digital signal received from the pulse sequence server 18. The received NMR signal is at or around the Larmor frequency, and this high frequency signal is down converted in a two step process by a down converter 208 which first mixes the NMR signal with the carrier signal on line 201 and then mixes the resulting difference signal with a reference signal on line 204. The down converted NMR signal is applied to the input of an analog-to-digital (A/D)

converter 209 which samples and digitizes the analog signal and applies it to a digital detector and signal processor 210 which produces 16-bit in-phase (I) values and 16-bit quadrature (Q) values corresponding to the received signal. The resulting stream of digitized I and Q values of the received signal are output to the data acquisition server 20. The reference signal as well as the sampling signal applied to the A/D converter 209 are produced by a reference frequency generator 203.

During the data acquisition window of a pulse sequence the transmit/receive switch is in its "receive" state and the coupling of the NMR signals from the coil elements 230 in the coil array 100 to their corresponding receive channels occurs in the usual fashion. When the transmit/receive switch 152 is in its "transmit" state a signal on control line 220 enables a set of isolation circuits 222 and a decoupling control circuit 224. As will be described in detail below, the isolation circuits 222 operate to protect the inputs to the receive channels 207 from currents induced in the coil array 100 during the transmit phase.

The decoupling control circuit 224 produces a bias current for each coil element in the coil array 100. The amount of each bias current is determined during a calibration scan. The decoupling control circuit 224 decouples each coil element from the transmit $B_1$ field in a controllable way to introduce a variable impedance into the coil loop at the match capacitor. The desired bias current levels are downloaded through input 226 from the pulse sequence server 18. The resulting decoupling bias currents are applied to corresponding coil element decoupling circuits 228. As will be described in detail below, the individual rf coil elements in the coil array 100 may be controllably decoupled in such a manner as to alter or shim the rf field produced during the transmit phase by the whole body coil 34 such that it is homogeneous within the subject being imaged or so that RF energy is focused into a particular region of interest and shape.

The coil array 100 described above is exemplary of a coil array in which its coil elements 230 are mounted to a substrate having non-zero Gaussian curvature. This structure may be altered by changing the number of coil elements 230 in the array 100 or by altering the shape of the supporting substrate. The following discussion describes how such coil arrays are constructed in accordance with the present invention.

There are many geometric options for arranging coil elements in an array on a surface that has non-zero Gaussian curvature to produce a reduced mutual inductance among the coils. In these geometries, the coil elements overlap over the entire region of interest to reduce the mutual inductance among the coils. Thus, the coil elements may have different orientations with respect to the static magnetic field. If the region of interest is, e. g., the head of a patient lying down in a magnetic resonance scanner, the array includes some coil elements whose normal axis is not substantially perpendicular to the z-axis of the scanner (i. e., the axis in the direction of the static magnetic field). For example, in some embodiments, the array includes coil elements that have a normal axis (i. e., axis normal to the plane of the coil) that is less than 60 degrees from the z-axis. In some embodiments, the array has a coil element whose normal axis is substantially parallel to the z-axis.

At least some of the individual coil elements of a coil array over a surface with non-zero Gaussian curvature can have positions and normals which correspond to the positions and normals of faces of a portion of a polyhedron, while allowing all coils to overlap with their nearest neighbors such that their mutual inductance is minimized. In some embodiments, the arrangement of coil elements may not correspond exactly to a particular polyhedron and/or may include some warping or distortion of the polygonal faces, but still allow for individual coil elements to be placed on a curved surface in a way that reduces mutual inductance among the coil elements. Some embodiments use particular polyhedra that have properties that are particularly useful for arranging coil arrays. For example, some convex polyhedra having regular convex polygonal faces (e. g., the Platonic Solids and Archimedean Solids) have faces that have an identical geometrical relationship to each neighboring face. This property allows an optimal coil element size chosen for one coil element to apply to other coil elements of the same type.

Polyhedra such as the Platonic Solids (e. g., the dodecahedron) or the Archimedean Solids (e. g., truncated icosahedron) provide patterns of polygons for overlapping coil elements to cover a portion of a spherical or near spherical surface, such as the head. For example, the center and normal of at least some of the coil elements in a coil array can correspond to the center and normal of a face of the polyhedron. For some polyhedra, such as polyhedra having faces that are regular convex polygons where no more than three faces meet at each vertex, coil elements can be arranged to cover a spherical or near spherical surface while maintaining near critical overlap between adjacent coil elements.

Another useful property occurs for polyhedra that have a large number (e. g., at least twelve) of faces. This property allows adjacent faces to have a small angle between them so that neighboring coil elements can be nearly co-planar.

In one example, a dodecahedron covers a complete sphere with twelve identical pentagonal faces. A hemispherical coil array can be constructed with approximately six to eight individual coil elements, each having a center coincident with the center of one of the pentagonal faces of a dodecahedron. In this example, each coil element has an identical shape (e. g., a circle or a pentagon) and an identical size chosen to provide the critical overlap between all adjacent coil element pairs.

Figure 5:
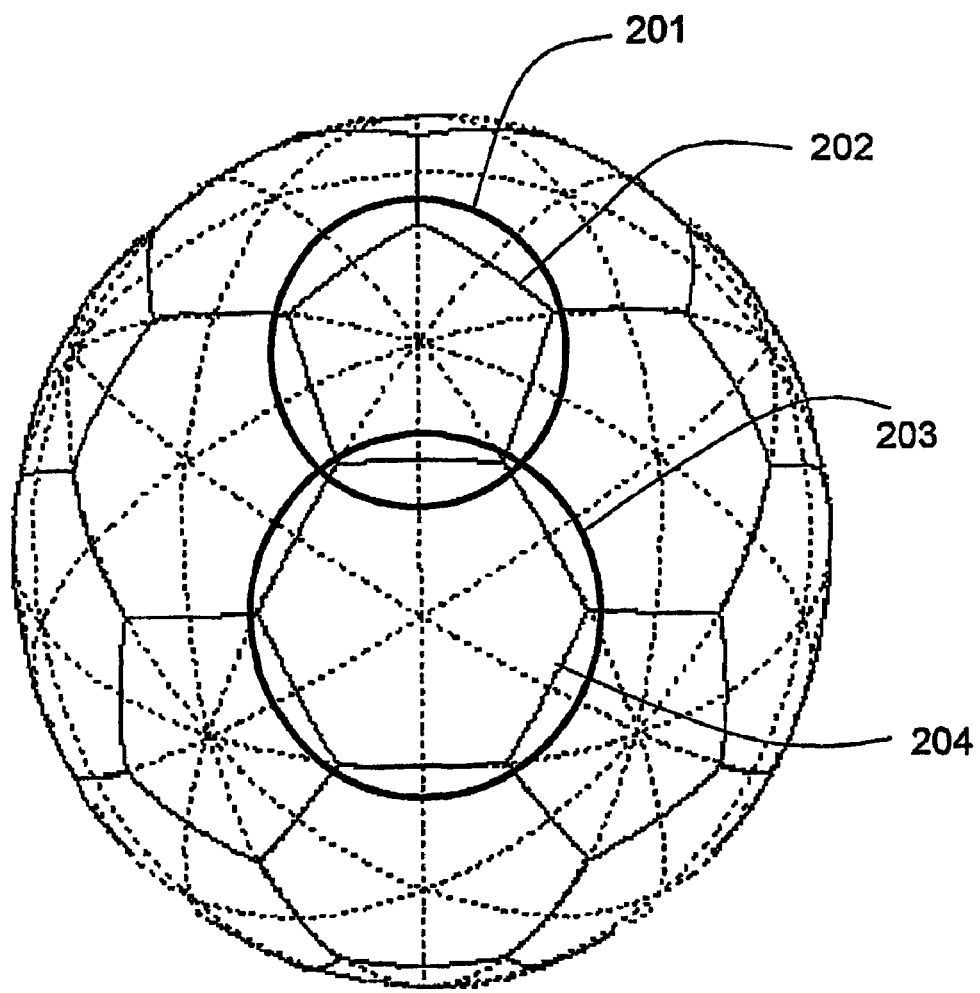
FIG. 5 is a pictorial view of an alternative spheroid coil array.

In another example, to incorporate more individual coil elements in a spheroid coil array, a truncated icosahedron (a "soccer ball" shape) arrangement can be used. In such an arrangement, there are twelve pentagonal faces and twenty hexagonal faces over a complete sphere (thirty-two faces in all). As shown in FIG. 5, individual coil elements can be arranged centered on the centers of the faces of a portion of a truncated icosahedron that corresponds to the size of the sample object 140. The circumference of a circle circumscribing a pentagonal face is approximately 0.85 times the circumference of a circle circumscribing a hexagonal face. One arrangement of coil elements in the coil array uses two different sizes of circular coil elements whose relative dimensions are close to this relationship. A first coil element 201 centered on a pentagonal face 202 has a circumference that is approximately 0.85 times the circumference of a second coil element 203 centered on a hexagonal face 204. The absolute sizes of the coil elements are chosen to obtain the critical overlap between the coil elements. A hemispherical coil array can be constructed with approximately sixteen to twenty coil elements.

Sections of the truncated icosahedron arrangement can be used to cover portions of regions of interest in an array for imaging surfaces that resemble a sphere over a particular area of the surface, e. g., the top of the head. A portion of the truncated icosahedron consisting of one pentagon attached to two, three, four or five hexagons (a "soccer-ball sub-unit") is inherently "bowl shaped" and provides non-zero Gaussian curvature to the array. Areas between these sub-units can be tiled with hexagons to form one continuous lattice which defines positions where coil elements can be placed and achieve reduced or minimized mutual inductance. Given a surface on which it is desired to arrange surface coils into an array, if the curvature of the surface locally is less than that of the soccer-ball sub-unit, a new sub-unit may be defined which is derived from the soccer-ball sub-unit by displacing the pentagonal tile until it lies close to the surface, thereby distorting slightly the surrounding hexagonal tiles. Coil elements placed over these distorted hexagons can be distorted similarly to achieve reduced or minimized inductive coupling to neighboring coils.

Other polyhedra can provide a basis for arranging coil elements of a coil array, and more than two sizes of coil elements may be included. In another example, the rhombicosidodecahedron (also known as the "small rhombicosidodecahedron"), which has sixty-two faces over a complete sphere, with pentagonal, square and triangular faces, can be used. A coil array using this arrangement would use three different coil element sizes, corresponding to each of the types of faces. Another useful property occurs for polyhedra that have faces of similar size (e. g., the ratio of the circumferences for two different types of faces is between 3/5 and 5/3, as in the examples described above). This property allows sensitivity to be more uniform over the coil array (since sensitivity tends to vary with coil element size).

A coil element need not have a shape that is precisely a circle or straight-sided polygon. For example, a coil element can have a shape that is derived from a pentagon by replacing the straight sides of a pentagon with arcs or lines having curves. As long as five-way symmetry of such a coil is preserved in a way which provides overlap to minimize mutual inductance, such coil elements can also be useful. A generalized tiling of pentagons and hexagons, some of which can be irregular, i. e., have sides of different lengths, can be useful to cover a curved shape.

As described above, faces of a portion of a polyhedron can be used to arrange at least some of the individual coil elements of a coil array over sample objects with non-zero Gaussian curvature, e. g., in an overlapping arrangement. Two or more "sub-arrays" of coil elements (e.g., a pentagon with five surrounding hexagons) can be combined by overlapping neighboring coil elements in the sub-arrays to form a coil array with a desired shape.

Figure 6:
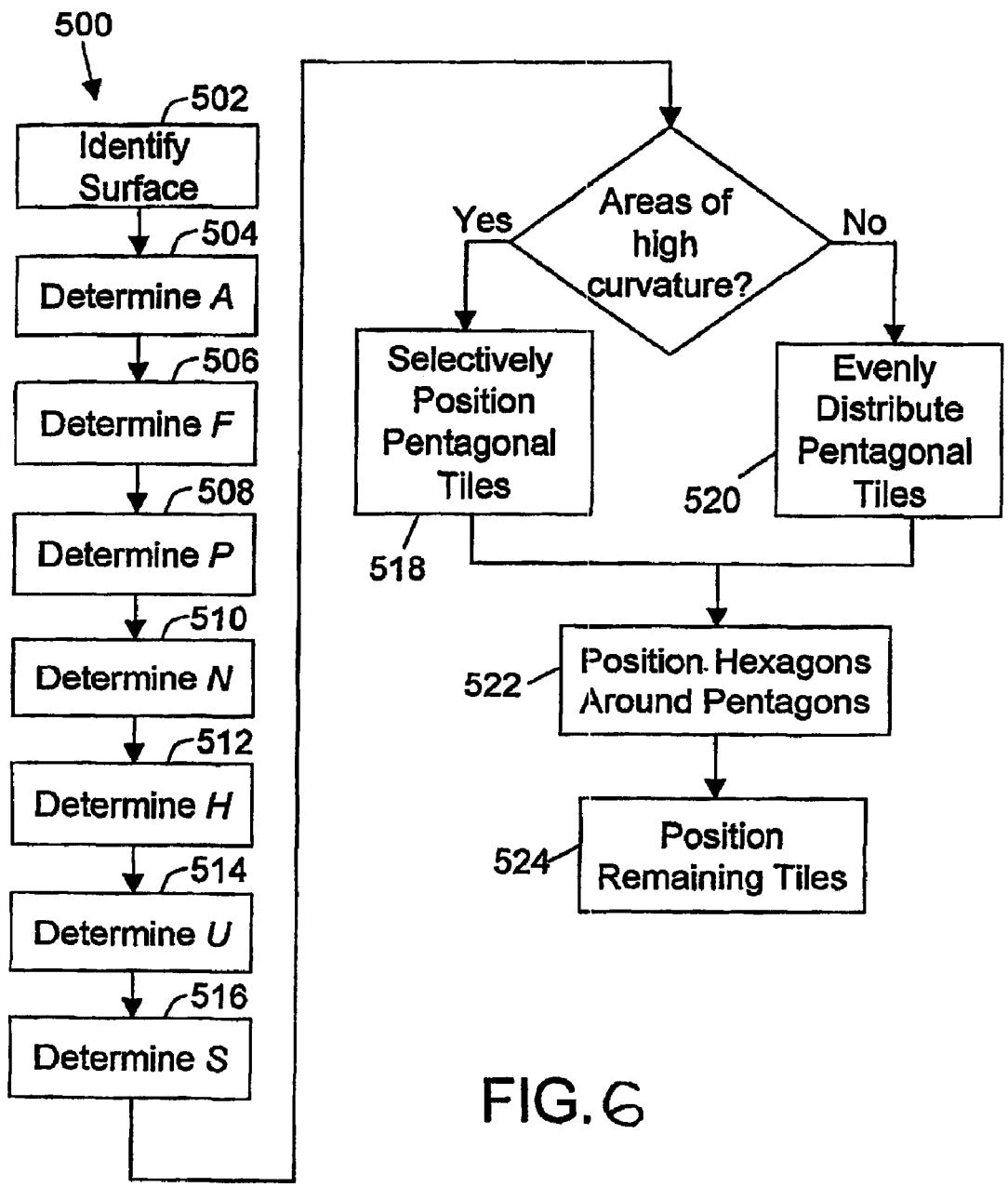
FIG. 6 is a flow chart illustrating the steps used to design a coil array according to the present invention.

FIG. 6 shows a flowchart for an exemplary procedure 500 to construct a coil array to cover a portion of a sample object with non-zero Gaussian curvature. A surface to be covered by the coil array is identified 502. After the surface is identified, the surface area A of the surface is determined 504 (e. g., from direct measurements of a sample object or calculated estimates). A "fractional curvature" F of the surface is also determined at 506, by comparing the surface to a complete sphere (F=1). For example, a coil array for imaging a head may use a surface corresponding to a hemisphere or half of a sphere with F=0.5. A coil array for imaging a shoulder may use a surface corresponding to a quarter of a sphere with F=0.25.

In this procedure 500, the arrangement of individual coil elements is based on combining pentagonal tiles and hexagonal tiles. Adding a pentagonal tile to a hexagonal array introduces a Gaussian curvature of approximately 12 degrees. A complete sphere can for example be covered with twelve pentagonal tiles and twenty hexagonal tiles (arranged as a truncated icosahedron). The procedure 500 includes determining at 508 an approximate number of pentagonal tiles P to be used for the selected surface: P=12×F. This number can be rounded up or down to the nearest integer. For a hemispherical coil array, P=12×0.5=6. The procedure 500 also includes determining at 510 a number of detector channels N that are available. An approximate number of hexagonal tiles H to be used for the selected surface is determined at 512 based on this number of channels N: H=N−P.

These quantities are used to determine 514 a "unit-tile surface area" U as follows:

$$U=(H\times 2.598)+(P\times 1.720).$$

The quantity 2.598 is the approximate area of a hexagonal tile with sides of length 1. The quantity 1.720 is the approximate area of a pentagonal tile with sides of length 1. For an approximately hemispherical head coil array with 96 channels (N=96), for example, the unit-tile surface area is $$U=(90\times 2.598)+(6\times 1.720)=244.14.$$

A scaling factor S is determined at 616 as the ratio S=A/U. The length of the sides of the pentagonal and hexagonal tiles used to cover the selected surface for arranging coil elements is L=√S. Using a calculated surface area A=107,832 mm$^2$ for a 96-channel head coil array, the tile side length L=21.02 mm.

After the number and size of tiles is determined, a model for the coil array can be constructed (e. g., using paper, plastic, or other materials), or a model for the coil array can be designed using three-dimensional computer-aided design (CAD) software or other computer graphics tool. For example, if the selected surface has portions having relatively high curvature compared to the rest of the surface, the procedure 500 includes positioning at 518 some of the pentagonal tiles near locations having relatively high curvature, such as near the top of the head in the coil array of FIG. 4. If the surface has a relatively uniform curvature, then the pentagonal tiles should be evenly distributed at 520 over the surface. Starting with one pentagonal tile, some hexagonal tiles are positioned edge-to-edge at 522 around it in an arrangement that corresponds to a portion of a truncated icosahedron. Depending on the shape of the surface, the hexagonal tiles may be deformed (e. g., bent or warped) to fit into place. Some hexagonal tiles are positioned edge-to-edge between other hexagonal tiles. Additional hexagonal tiles are added to the tiling pattern until the position of another pentagonal tile is approached.

The final position and orientation of each additional pentagonal tile incorporated into the tiling pattern will typically have to be adjusted so that it can match edge-to-edge with the tiles already placed. Any remaining pentagonal or hexagonal tiles can be positioned at 524 in the model (and deformed if necessary) in a way such that the model conforms to the local curvature of the selected surface as closely as possible. If the only deformations are warping of the tiles such that the lengths of the sides remain the same, the overall size and shape of the tiles will remain almost unchanged compared to flat regular hexagons or pentagons, simplifying the coil placement procedure. If the curvature of the "soccer-ball element" is much higher than the local curvature of the surface, the tiling pattern may not conform as closely to the surface as desired. In this case, the pattern can be mapped onto the surface, effectively moving a tile that is not close enough to the surface inwards or outwards until it lies on the surface, which requires shortening some of the sides of some of the tiles. While tiles distorted in this way may not be identical in size and shape to regular hexagons or pentagons, they can still provide the basis for a coil array with reduced or minimized mutual inductance between neighboring coils.

Such a model can serve as a guide for positioning the coil elements used for the coil array. The individual coil elements can be constructed from a combination of conductive material and capacitors. For example, a loop of circuit board or copper tape is broken in several places and these breaks are bridged with capacitors. The resulting effective inductance and capacitance of the loop determine the resonant frequency of the loop. This resonant frequency is tuned to the operating frequency of the MRI system 100 (e. g., 63.4 MHz for a system using a 1.5 Tesla magnetic field source, or 123.3 MHz for a system using a 3 Tesla magnetic field source).

The coil elements are arranged with their respective centers aligned with the center of a tile. The relative sizes of the coil elements are selected to correspond to the relative sizes of the tiles, and in the preferred embodiment the absolute size of the coil elements is selected to provide a coil element overlap close to the critical overlap, as described above. The shape of a coil element can be round, or alternatively, the shape of a coil element can correspond to the shape (e. g., pentagonal or hexagonal) of the tile according to which it is placed. The shape of a coil element may also be deformed to match the model. The exact position and/or shape of the coil elements can optionally be optimized empirically or by computer modeling to match the surface well and maintain reduced mutual inductance among the coil elements.

There are applications where the coil elements are positioned as described above, but their size is selected such that they do not overlap their neighbors. In one embodiment the coil elements are reduced in size such that a gap occurs between them and their neighbors. Such a structure does not minimize mutual inductance between coil elements and the coupling must be mitigated using preamplifier decoupling. The advantage of such a "gapped" coil array is that the sensitivity profiles of each coil element are more distinct, which improves the performance of an accelerated imaging technique such as SENSE, SMASH and GRAPPA.

Another embodiment of the coil array employs coil elements that are centered on their underlying polygonal tiles and have the shape of their underlying tiles. In this embodiment the coil elements are sized to approximate the size of the underlying tiles, which means the adjacent coil elements are very close to one another and the mutual inductance is relatively high. In this embodiment preamplifier decoupling is not sufficient and decoupling is achieved by inductive or capacitive elements that lie on shared coil element edges.

Other procedures for arranging the coil elements of a coil array over sample objects with non-zero Gaussian curvature are possible. For example, other tile shapes (e. g., triangles, squares, octagons) can be used to generate a model of a surface based on portions of a polyhedron having an appropriate shape (i. e., a shape that allows coil elements to be positioned as close as possible to the selected surface). Coil elements can be arranged on a surface that has locally negative Gaussian curvature (a saddle shape) by incorporating a heptagonal (7-sided) tile at the points of maximum negative curvature.

Some sample objects may have a surface with a complex form that includes multiple curved features. The procedure 500 described above can be used to generate multiple models for the various features. The models can then be connected by matching edges of polygonal tiles. For example, a model for a coil to cover a patient's shoulder and neck may include a first portion curved in one direction to cover the shoulder and a second portion connected to the first portion curved in a different direction to cover the neck. Other complex forms may include relatively flat surfaces. For example, a model for a coil to cover a patient's knee may include one or more curved portions to cover the top of the knee and two flat portions connected to the curved portions to cover the sides of the knee.

Figure 7:
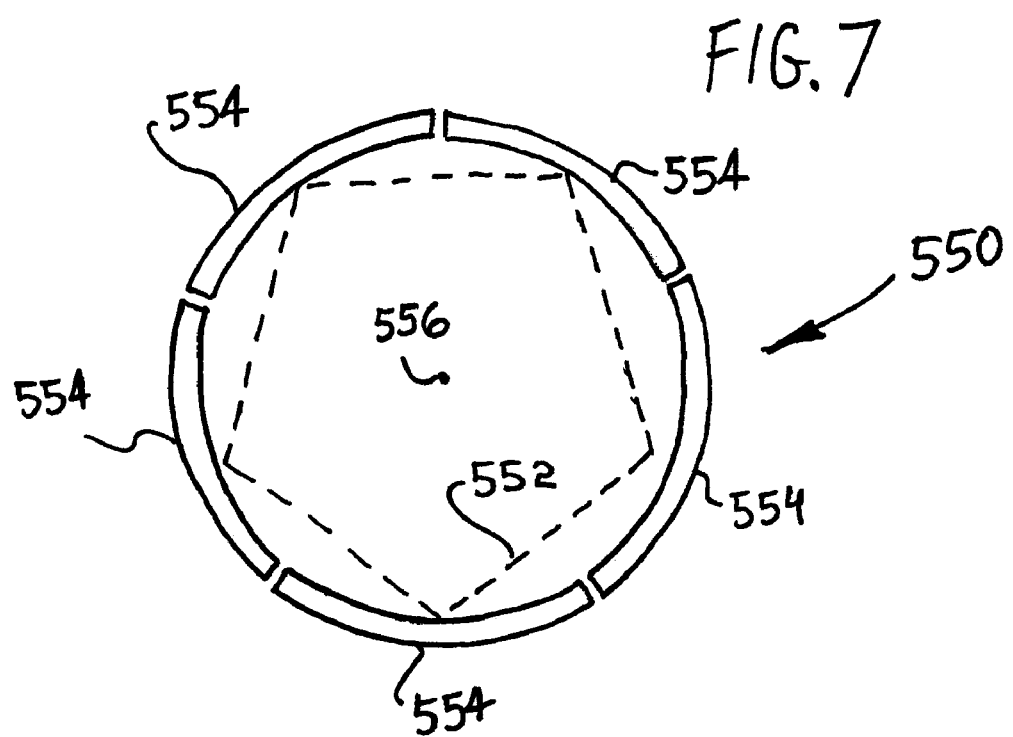
FIG. 7 is a pictorial view of a single coil element.

Coil elements can be manufactured using a number of different methods. As shown in FIG. 7, for example, a single coil element 550 associated with a pentagonal tile 552 is a loop comprised of five conductive segments 554 that form a circular pattern around the pentagonal tile 552 and concentric with the tile center 556. Capacitors (not shown in FIG. 7) connect the conductive loop segments 554 together and the values of these capacitors is selected to tune the coil element to the desired frequency. The NMR signal is output through a pair of wires connected across one of these capacitors as will be described in more detail below.

Figure 8:
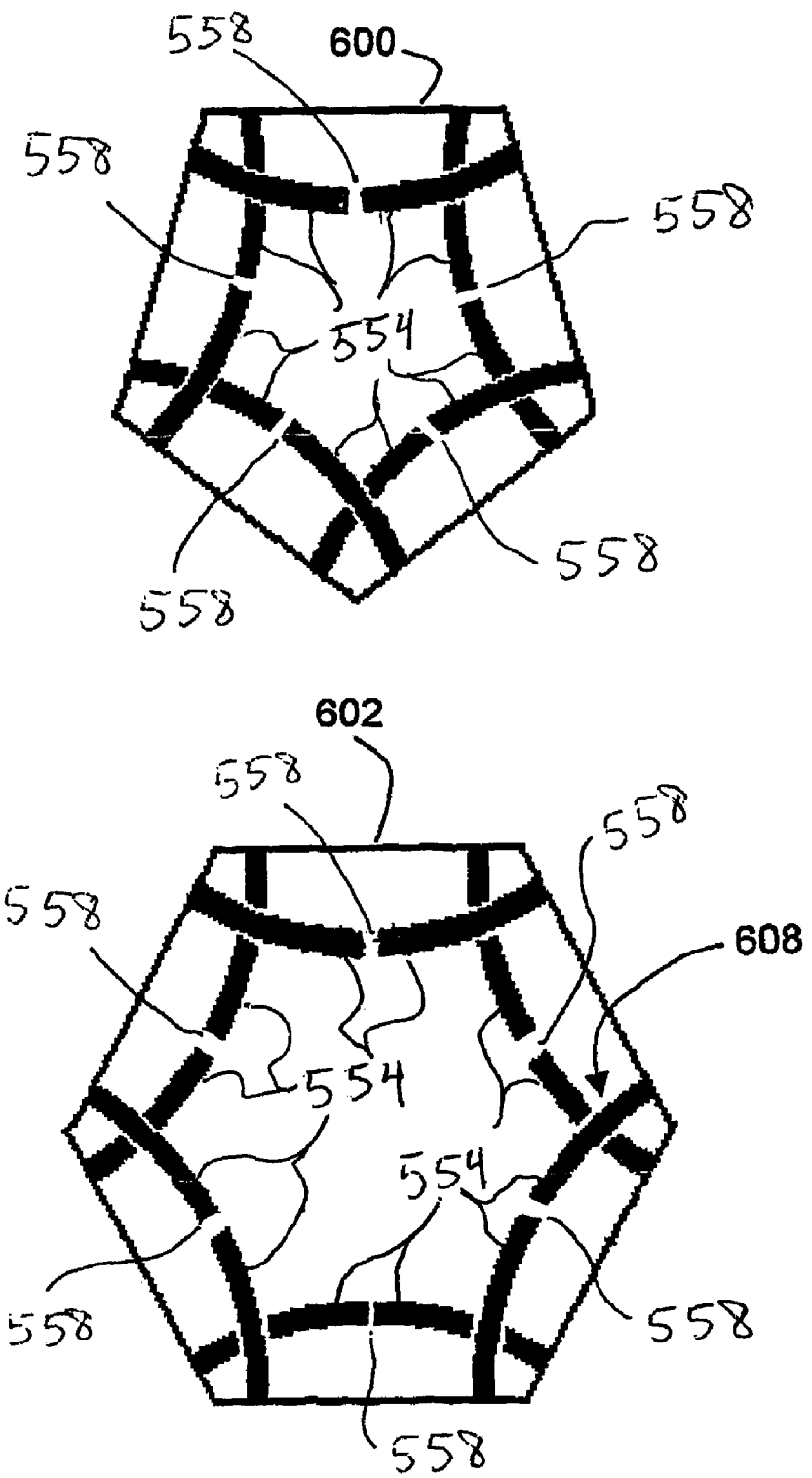
FIG. 8 is a pictorial view of a printed circuit board version of a pentagonal tile and a hexagonal tile in a coil array which when assembled, forms conductive paths for the various coil elements.

When the size of the tiles and their associated coil elements is relatively large (e.g., 3 cm or larger on a side) it is advantageous to form the conductive loop segments 554 as a copper layer on an insulating substrate using printed circuit board technology. As shown in FIG. 8, printed circuit boards 600 in the shape of a pentagonal tile and printed circuit boards 602 in the shape of a hexagonal tile may be produced and combined together to form a coil array. Each circuit board tile 600 and 602 contains portions of the conductive segments 554 for the coil elements associated with surrounding tiles. When assembled into a coil array, the ends of each conductive segment 554 are connected to the ends of conductive segments in adjacent circuit board tiles and capacitors are soldered in place to span the gaps 558. The intersections of coil segments, such as that indicated at 608, are insulated from one another either in the printed circuit board manufacturing steps or by breaking one of the conductors 554 and soldering a jumper wire which is spaced above the crossing coil segment 554. A shaped coil array is formed by assembling the pentagonal tiles 600 and hexagonal tiles 602 together in a pattern which enables the resulting coil array to follow the desired complex contour.

Figure 9:
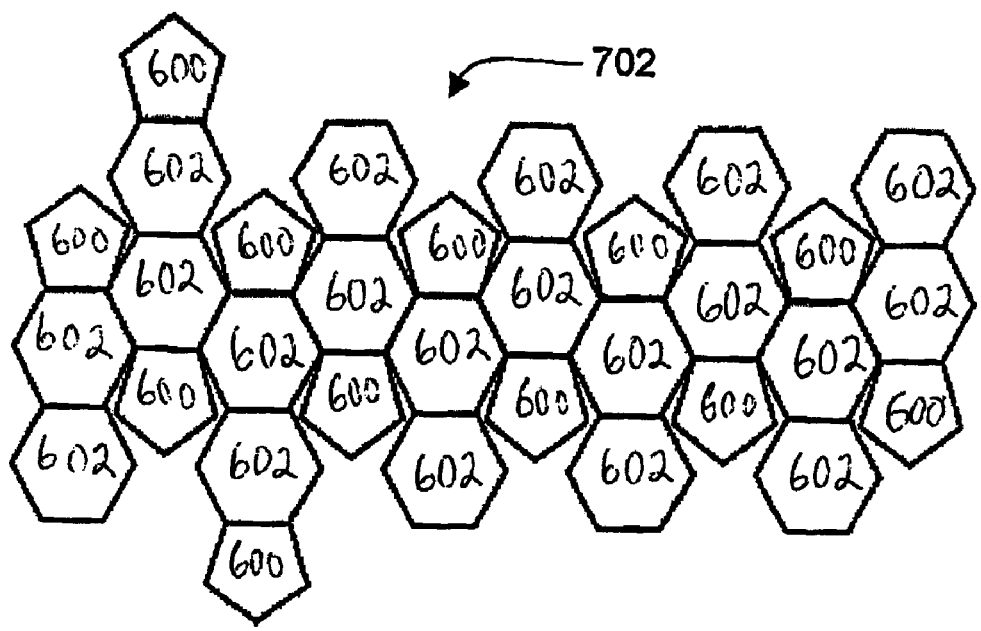
FIG. 9 is a pictorial view of a printed circuit board which can be folded to form a coil array of a complex shape.

It is also possible to produce the coil array as a single printed circuit board. Referring to FIG. 9, a single flexible printed circuit board 702 may be produced with hexagonal circuit board patterns 602 and pentagonal circuit board patterns 600 joined together as shown. This saves considerable assembly time since the conductive segments 554 on tiles that are contiguous may be connected together in the printed circuit board process. The flexible circuit board 702 is folded to the desired contour by bringing the sides of tiles that are not contiguous with each other close together. The remaining unconnected conductive segments in adjacent tiles are then soldered together. In this case the tuning capacitors may be mounted in place using automated equipment before the circuit board 702 is folded into its final shape.

Another coil array structure that may be constructed according to the present invention can be described as a "chain mail" coil array. Referring particularly to FIG. 12, a chain mail coil array 900 designed for shoulder imaging is comprised of an array of coil elements 902 that are fastened together with fasteners such that they drape over the subject's shoulders. As shown in FIGS. 13 and 14, the coil elements 902 are joined to each other using rivets 904 at points where adjacent coil elements overlap such that they are retained together in an array with the proper overlap between adjacent coil elements 902. The rivets 904 do not tightly fasten coil elements 902, but instead allow enough movement therebetween such that the coil array 900 will drape over the subject and lie close to the surface of the subject.

The proper sizing and positioning of the coil elements 902 in this chain mail coil array is determined using an underling array of hexagonal and pentagonal tiles as described above. More particularly, the polygonal tiles are drawn on a model of the subject to be imaged (e.g., shoulder) using pentagonal tiles where Gaussian curvature is highest. Coil elements 902 are then centered on each polygon and riveted together. The resulting coil array 900 will take many shapes, but when it is draped over the selected anatomy, it will assume a shape of optimal coil element overlap in which each coil element 902 is free to rest against the surface of the subject.

It has been discovered that when the size of each coil element is very small (e.g., less than 3 cm on each polygon side) it is preferable to form the conductive coil elements using circular-shaped wire rather than conductive circuit board layers. More specifically, wire conductive elements made from 16 awg copper wire are bent to substantially circular shape and cut to form a circular coil element having two gaps into which tuning capacitors are mounted. These wire coil elements are placed over an insulating substrate formed with the desired contour and positioned thereon using an array of polygonal tiles drawn on the surface of the contoured substrate. As described above, a circular coil element is positioned concentric about the center of each tile. Eddy current losses are reduced in this "wire" version of the coil array resulting in a higher coil array SNR.

Figure 3:
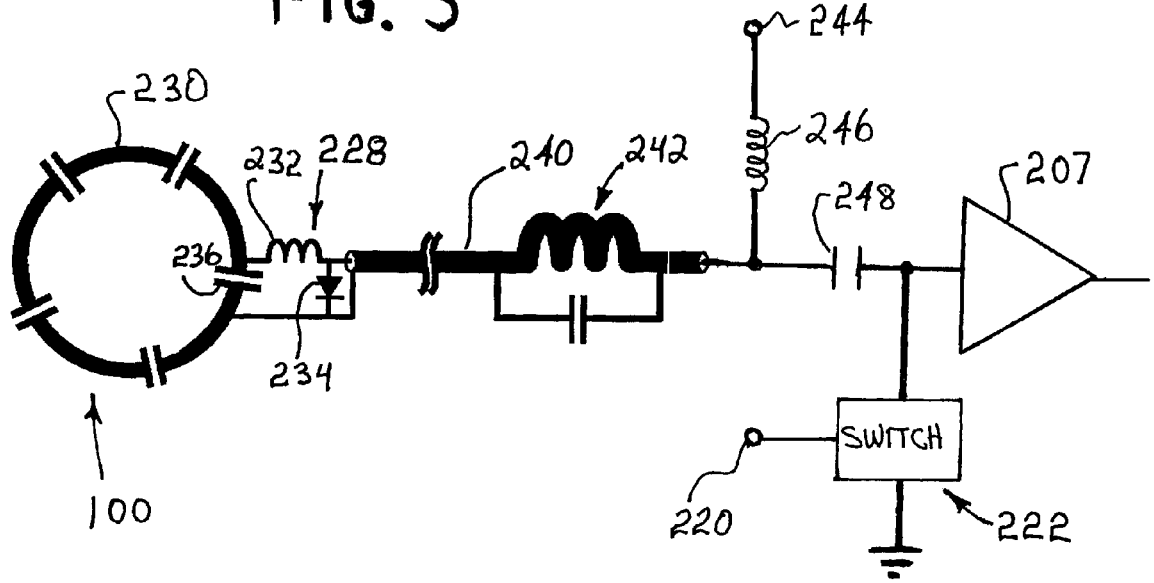
FIG. 3 is an electrical schematic diagram of a first embodiment of an input circuit for each coil element in the circuit of FIG. 2.

Referring particularly to FIG. 3, one circuit for connecting one coil element 230 in the coil array 100 to its receive channel input 207 is shown. The coil element 230 has inductive and capacitive elements that form a resonant circuit that is tuned to the system Larmor frequency. A decoupling circuit 228 comprised of inductor 232 and diode 234 connects across one capacitive component 236 in the coil element 230, and when the diode 234 is forward biased by a bias current, the inductor 232 is effectively connected in parallel with the capacitor 236 to decouple the coil element 230. This is normally done during the transmit phase of the pulse sequence in order to prevent the coil element 230 from interfering with the homogeneous $B_1$ field being produced. This decoupling function may also be used in a controlled manner to intentionally alter the $B_1$ field being produced to improve its homogeneity.

The decoupling elements 232 and 234 are physically mounted on the coil array 100 and are connected by a coaxial cable 240 to the receiver circuit board (not shown in the drawings). A cable trap 242 is formed by the cable 240 to convert a balanced signal to an unbalanced signal and block common mode cable currents. A bias current input 244 from the decoupling control circuit 224 connects through an inductor 246 to the center conductor of coaxial cable 240 and a coupling capacitor 248 connects the center conductor to the receive channel input 207. A switch 222 also connects the receive channel input 207 to circuit ground and the switch 222 is operated by transmit/receive switch control line 220 to ground the receive channel input 207 during the transmit phase of a pulse sequence.

During the transmit phase when an rf field is being produced by the whole body coil 34 or other transmit coil apparatus, the coil element 230 is decoupled in a controlled amount by the bias current input at 244. The inductor 246 blocks rf signals from reaching the decoupling control circuit 244. At the same time, switch 222 is operated through control line 220 to ground the receive channel input 207 to protect it from rf voltages induced in the partially decoupled coil element 230.

When small coil elements are employed in the coil array it is also important to maximize the decoupling of each receiver channel input. As indicated above, mutual inductance between adjacent coil elements may be minimized by judiciously overlapping the coil elements. However, when the size of each coil element is reduced, the capacitor value needed to match the sample impedance to the 50 Ohm system becomes large. If this capacitor is also used to form the decoupling circuit, the Q of the decoupling circuit is reduced, which reduces the effectiveness of both the PIN diode detuning and the preamp decoupling effect. Improved decoupling is achieved in this case by using the alternative input circuit illustrated in FIG. 10. This is similar to the input circuit described above and shown in FIG. 3 except the decoupling functionality and the impedance matching functionality are separate to increase the Q of the decoupling circuit and hence increase the strength of the preamplifier decoupling. More specifically, a decoupling circuit comprised of inductor 720 and diode 722 is connected across one of two capacitors 724 in the conductive wire loop that forms the coil element 726. This circuit operates as described above to decouple the coil element when the diode 722 is forward biased by a current.

Figure 10:
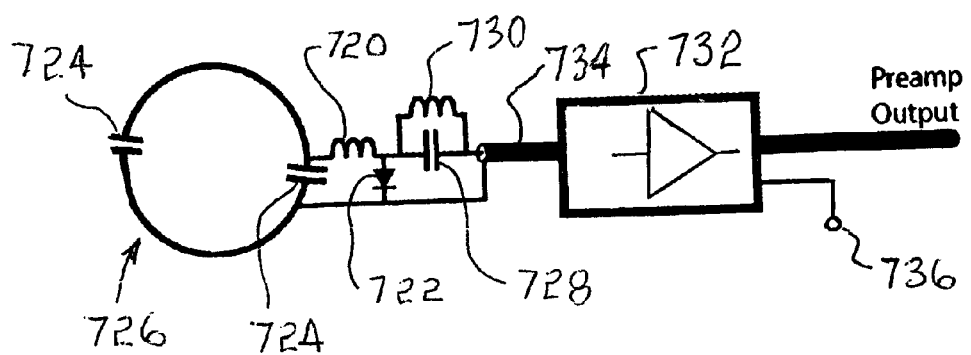
FIG. 10 is an electrical circuit diagram of an alternative input circuit for a coil element.

The second embodiment of the input circuit in FIG. 10 also includes a series circuit comprised of capacitor 728 which matches the impedance appearing across the capacitor 724 in the coil element 726 to the 50 Ohm system impedance and an inductor 730 which blocks RF but provides a dc path for the PIN diode bias current. All of the components for both the decoupling circuit and the impedance matching circuit are mounted on the array coil and they connect to the preamplifier input through a 5 cm long piece of coaxial cable 734. The preamplifier in this case is made by Siemens Medical Solutions and it includes a built-in cable trap and bias current input line 736. In some instances the impedance which must be presented to the input of the preamplifier to achieve the best noise performance is higher than 50 Ohms, allowing the standard combined match/decoupling circuit to be used without requiring an excessively high capacitor value in the match circuit.

Figure 11:
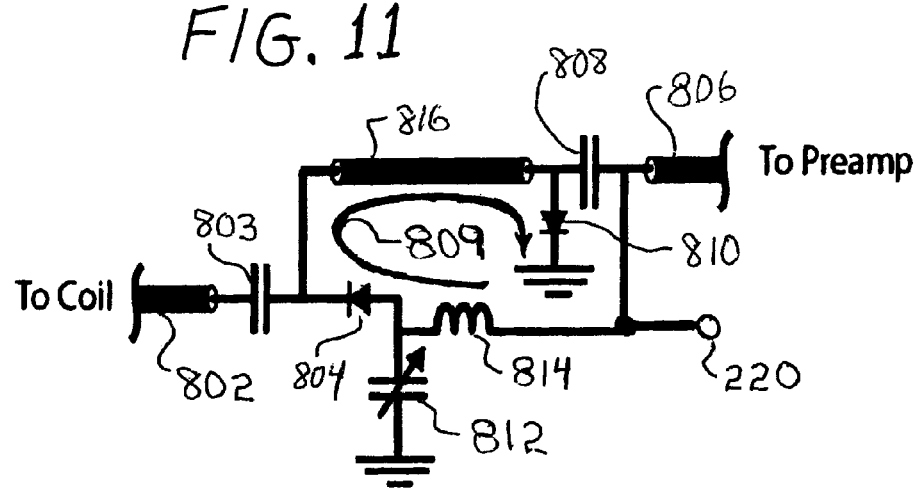
FIG. 11 is a circuit diagram of a third embodiment of an input circuit for each coil element in the circuit of FIG. 2.

Yet another preferred embodiment is the addition of the circuit shown in FIG. 11. This circuit is characterized by the fact that it can be used to control the degree of coupling between the receive element and the transmit RF field, allowing manipulation of the transmit RF field, and that it can achieve this without the need to mount any additional components on the coil structure. The placement and operation of the circuit function as follows. Normally the phase length of the RF signal path between the detuning circuit on the coil element and the preamp is chosen such that the input impedance of the preamp is transformed into a low impedance (virtual short) at the coil element detuning circuit, creating the preamp decoupling effect, where by current flow in the receive element is minimized. The circuit of FIG. 11 is constructed such that the phase length of the receive path between 802 and 806 is a multiple of 180 degrees. This allows the preamp decoupling effect to apply as usual during the reception of the MR signal.

During transmit, the diodes 804 and 810 are forward biased by applying a positive voltage to terminal 220, putting the diodes into a conducting state. A choke 814 blocks the AC signal while enabling the bias current flow 809. The diode 810 thus creates a short circuit across the receive path. The coax 816 has a phase length of one quarter of the wavelength at the MR frequency, and therefore, transforms the low impedance of the short circuit at diode 810 into a high impedance at the other end of the coax 816, blocking any RF signal from entering the coax 816 during the transmit phase. At the same time the shunt diode 810 effectively grounds the preamp input 806 during the transmit phase of operation. The coax from the coil element (802) is connected instead via the diode 804 to the variable capacitor 812 which is connected to ground, creating a high impedance termination. The phase length between this termination and the detuning circuit on the coil element is chosen such that the high impedance at the termination is transformed into a low impedance (virtual short) at the detuning circuit, creating a similar effect to that which is achieved with preamp decoupling. If the phase length between the termination 812 and the coil detuning circuit is an odd multiple of one quarter wavelength, a high impedance will be created by the coil detuning circuit, limiting the current which can flow in the coil element and limiting the extent to which the transmit RF field is able to excite current in the coil element. By adjusting the variable capacitor 812 the phase length may be adjusted, allowing the current limiting effect to be weakened or strengthened, allowing the degree of coupling between the transmit RF field and the receive coil to be varied from −22 dB to 0 dB. This control allows the receive coils to be used to focus the transmit RF field into regions near each receive element and thus achieve "RF shimming". With control of each element in a 32 channel array, for example, it is possible to create a transmit RF field with the desired uniform distribution and hence overcome the problems of RF inhomogeneity at high magnetic fields, or to focus RF to only a particular region of interest.

The receive path through the circuit of FIG. 11 is enabled by applying a reverse bias to the diodes 804 and 810 by applying a negative voltage to the terminal 220, causing the diodes to be non-conducting. The tuning capacitor 812 is thus no longer connected to the input coaxial cable 802 and the input signal thereon is coupled through the coaxial cable 816.

In addition to providing a means for controlling the coupling of the coil element to the RF transmit coil during the transmit phase, this embodiment of the input circuit does not require that any circuit components be physically mounted on the coil element or its supporting structure. This can greatly simplify the construction of the coil array.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A magnetic resonance imaging coil array configured to acquire data from a subject having an exterior contour extending along multiple curves, the coil array comprising:
a plurality of conductive coil elements, wherein the coil elements are arranged so that their centers are aligned with the centers of corresponding polygons that define contiguous regions on a supporting structure, configured to substantially contour the surface of the subject having the exterior contour extending along multiple curves, and
wherein the structure has non-zero Gaussian curvature and the shapes of the polygons are selected such that the coil elements closely follow the contour of the supporting structure.

2. The coil array of claim 1 in which each coil element is formed by a loop of wire fastened to a substrate.

3. The coil array of claim 1, wherein each coil element overlaps at least one other coil element.

4. The coil array of claim 3, wherein each coil element overlaps with all adjacent coil elements.

5. The coil array of claim 1, wherein the coil elements are substantially the same size.

6. The coil array of claim 5, wherein the ratio of the circumferences of any two coil elements is equal to or greater than 3/5, and less than or equal to 5/3.

7. The coil array of claim 1, wherein the coil elements are formed on a substrate and the shape of the substrate is a helmet.

8. The coil array of claim 1, wherein the polygonal regions include a plurality of hexagonal polygons and at least one non-hexagonal polygon.

9. The coil array of claim 1, wherein the location of each coil element is based on a tiling pattern of regular polygons.

10. The coil array of claim 1, wherein each coil element is sized to fit within its corresponding polygonal region.

11. The coil array of claim 1, wherein at least one polygon is a pentagon.

12. The coil array of claim 1, wherein the polygonal regions comprise a combination of hexagonal and pentagonal regions.

13. The coil array of claim 1, wherein the supporting structure conforms closely to a surface of at least a portion of a human head.

14. The coil array of claim 1, wherein the polygonal regions comprise a combination of hexagonal, pentagonal and heptagonal regions.

15. The coil array of claim 1, wherein the polygonal regions comprise a geodesic tiling.

16. The coil array of claim 1 in which the conductive coil elements are connected together by a substrate.

17. The coil array of claim 1 in which the conductive coil elements are connected together by a flexible substrate.

18. The coil array of claim 4 in which the conductive coil elements are connected together by fasteners at points where adjacent conductive coil elements overlap.

19. A coil array configured for use in a magnetic resonance imaging (MRI) system in order to acquire signals from a region of interest in a subject, the combination comprising:
a substrate having a surface shaped in order to curve around the region of interest extending in a plurality of curves and having a non-zero Gaussian curvature from a location on the substrate;
a plurality of coil elements arranged on the substrate in an overlapping pattern that surrounds the region of interest;
wherein the overlapping pattern is based on a tiling pattern of regular polygons, each coil element is aligned at a center of one of said regular polygons and each coil element is sized in order to overlap adjacent coil elements such that the mutual inductance there between is minimized.

20. The coil array as recited in claim 19 in which the regular polygons include hexagons and a pentagon.

21. The coil array as recited in claim 19 in which the substrate is helmet-shaped in order to fit over the head of a subject, and the region of interest is in the subject's brain.

22. The coil array as recited in claim 19 in which each coil element is connected to a preamp with a length of cable chosen in order to transform the input impedance of the preamp into a low impedance at the coil element.

23. The coil array as recited in claim 19 in which each coil element is substantially circular.

24. The coil array as recited in claim 19 in which each coil element is connected to a separate preamplifier through an impedance matching circuit which transforms the input impedance of the preamp into a low impedance corresponding to the impedance at the coil element.

25. The coil array as recited in claim 24 in which a decoupling circuit is connected to each coil element.

26. The coil array as recited in claim 25 in which the decoupling circuit includes a diode through which a current flows in order to control the extent of the decoupling of the coil element.

27. The coil array as recited in claim 19 in which each coil element is a loop of wire attached to the substrate and it includes one or more capacitors connected in the loop.

28. The coil array as recited in claim 27 in which each coil element includes a decoupling circuit and elements of the decoupling circuit are attached to the substrate.

29. The coil array as recited in claim 19 in which each coil element is connected to a separate preamplifier through an input circuit, and the input circuit includes:

- a coaxial cable having one end connected to the coil element and another end connected through an impedance matching device to the preamplifier input;
- a diode coupled to the another end of the coaxial cable and a source of bias current;
- a tuning capacitor connected to the diode; and
- a shunt diode coupled to the preamp input;
- wherein a bias current is applied during a transmit phase in order to forward bias both the diode and the shunt diode and effectively shunt the preamplifier input into ground and effectively connect the tuning capacitor to said another end of the coaxial cable.

30. The coil array as recited in claim 29 in which the impedance matching device is a length of coaxial cable.

31. A method for configuring a coil array configured for use in magnetic resonance imaging, the steps comprising:

- a) forming an overlapping pattern of a plurality of polygonal coil element circuit boards on a flexible substrate;
- b) folding the flexible substrate in order to form a curved surface extending in a plurality of curves to substantially contour a surface of a subject extending in a plurality of curves having non-zero Gaussian curvature; and
- c) electrically connecting together adjacent circuit board patterns in order to form an array of overlapping coil elements, which is then utilized in magnetic resonance imaging.

32. The method as recited in claim 31 in which step c) is performed partially before step b) is performed and partially after step b) is performed.

33. The method as recited in claim 31 which includes mounting coil element circuit components on circuit board patterns before step b) is performed.

* * * * *